United States Patent [19]
Silvestrini

[11] Patent Number: 5,405,384
[45] Date of Patent: Apr. 11, 1995

[54] ASTIGMATIC CORRECTING INTRASTROMAL CORNEAL RING

[75] Inventor: Thomas A. Silvestrini, Alamo, Calif.

[73] Assignee: Keravision, Inc., Santa Clara, Calif.

[21] Appl. No.: 163,650

[22] Filed: Dec. 6, 1993

Related U.S. Application Data

[63] Continuation-in-part of Ser. No. 939,492, Sep. 9, 1992, abandoned.

[51] Int. Cl.⁶ ............................................. A61F 2/14
[52] U.S. Cl. ....................................... 623/5; 606/107
[58] Field of Search ............................ 623/5; 606/107

[56] References Cited

U.S. PATENT DOCUMENTS

| | | |
|---|---|---|
| 4,452,235 | 6/1984 | Reynolds . |
| 4,688,570 | 8/1987 | Kramer et al. . |
| 4,815,463 | 3/1989 | Hanna . |
| 4,941,093 | 7/1990 | Marshall et al. . |
| 4,951,744 | 10/1990 | Kilmer et al. . |
| 4,976,719 | 12/1990 | Siepser ................................. 606/151 |
| 4,994,081 | 2/1991 | Civerchia et al. ................... 606/107 |
| 5,067,961 | 11/1991 | Kelman et al. . |
| 5,089,443 | 3/1992 | Parel et al. . |
| 5,090,955 | 2/1992 | Simon . |
| 5,188,125 | 2/1993 | Kilmer et al. ........................ 606/107 |

FOREIGN PATENT DOCUMENTS 2095119 12/1981 United Kingdom .

*Primary Examiner*—Jerome L. Kruter
*Attorney, Agent, or Firm*—Morrison & Foerster

[57] ABSTRACT

This invention is an intrastromal corneal ring ("ICR") which is not uniform in dimension. It has, typically, two or more raised areas (or areas of additional bulk) spaced apart from each other on the ring. This ring design, when introduced into the stroma and properly adjusted there, permits at least partial correction of astigmatism in the eye.

26 Claims, 4 Drawing Sheets

ASTIGMATIC CORRECTING INTRASTROMAL CORNEAL RING

RELATED APPLICATIONS

This is a continuation-in-part of U.S. Ser. No. 07/939,492, filed Sep. 9, 1992 now abandoned, the entirety of which is incorporated by notice.

FIELD OF THE INVENTION

This invention is an intrastromal corneal ring ("ICR") which is not dimensionally uniform about the ring. It has at least one area, or, more typically, two or more raised areas (or areas of additional bulk) spaced apart from each other on the ring. This ring design, when introduced into the stroma and properly adjusted for position there, permits at least partial correction of astigmatism in the eye.

BACKGROUND OF THE INVENTION

Anomalies in the overall shape of the eye can cause visual disorders. Hyperopia ("farsightedness") occurs when the front-to-back distance in the eyeball is too small. In such a case, parallel rays originating greater than 20 feet from the eye focus behind the retina. In contrast, when the front-to-back distance of eyeball is too large, myopia ("nearsightedness") occurs and the focus of parallel rays entering the eye occurs in front of the retina. Astigmatism is a condition which occurs when the parallel rays of light do not focus to a single point within the eye, but rather focus to a region due to the fact that the cornea is aspherical and refracts light in a different meridian at different distances. Some degree of astigmatism in an eye is normal, but where the astigmatism is too pronounced, it must often be corrected.

Hyperopia, myopia, and astigmatism are usually corrected by glasses or contact lenses. Surgical methods for the correction of such disorders are known. These methods include radial keratotomy (see, e.g., U.S. Pat. Nos. 4,815,463 and 4,688,570) and laser corneal ablation (see, e.g., U.S. Pat. No. 4,941,093).

Another method for correcting those disorders is through the implantation of polymeric rings in the eye's corneal stroma to change the curvature of the cornea. Previous work involving the implantation of polymethylmethacrylate (PMMA) rings, allograft corneal tissue and hydrogels is well documented. One of the ring devices involves a split ring design which is inserted into a channel previously dissected in the stromal layer of the cornea. The device uses a minimally invasive incision through which the channel for the implant is created and, finally, through which the implant is inserted.

U.S. Pat. No. 4,452,235, to Reynolds, describes a method and apparatus for corneal curvature adjustment. The method involves inserting one end of a split end adjusting ring into the cornea of the eye and moving the ring in a circular path until its ends meet. The ends are thereafter adjusted relative to each other until the shape of the eye has assumed a desired curvature whereupon the ends are fixedly attached to maintain the desired curvature of the cornea.

Additionally, U.S. patent application Ser. No. 07/820,422, by Davenport et al., entitled "Method for Corneal Curvature Variation" suggests the use of ICRs for the correction of astigmatism. That disclosure does not suggest the use of ICRs having the inventive shape to alleviate astigmatism in the eye.

None of the prior art disclosures suggest the use of an ICR having a non-uniform shape about their periphery.

SUMMARY OF THE INVENTION

This invention is to a device, an astigmatic correcting intracorneal ring ("ACICR"), which is inserted into the interlamellar region of the eye's stroma. For the purpose of alleviating astigmatism, the device is an improvement over previously existing ICRs. Unlike other ICRs which have a constant cross section when viewed through various cross-sections of the ring, the inventive ACICR typically has at least one region in which the cross section is thicker or the bulk of that region is more pronounced. Often the rings will have two or more regions at which the bulk is increased. By proper alignment of the larger regions of the ACICR with the eye's anomalies, the astigmatism may be alleviated.

The devices for forming the intrastromal pathway into which these ICRs may be placed is well known.

DESCRIPTION OF THE INVENTION

Prior to explaining the details of the inventive devices, a short explanation of the physiology of the eye is needed to appreciate the functional relationship of the device to the eye.

Figure 1:
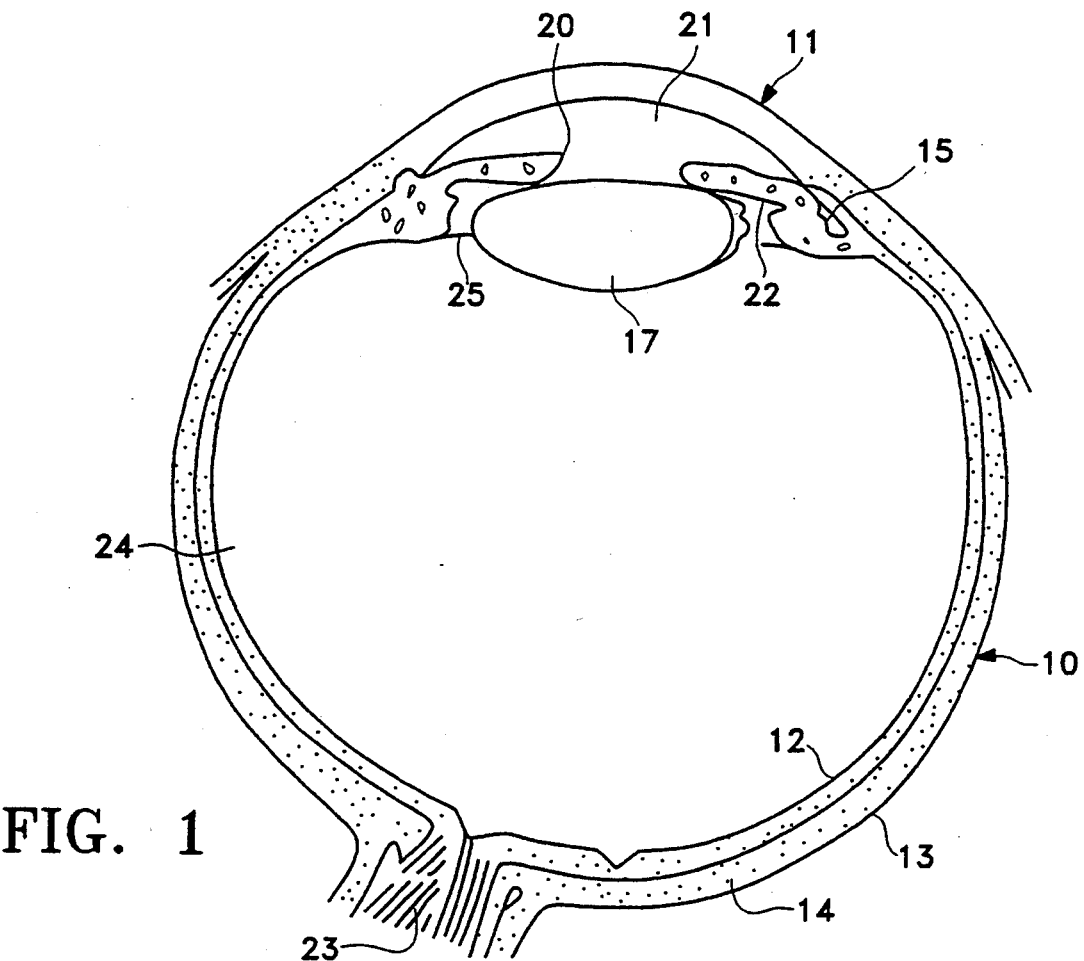
FIG. 1 is a schematic representation of a horizontal section of the eye.

FIG. 1 shows a horizontal section of the eye with the globe (10) of the eye resembling a sphere with an anterior bulged spherical portion representing the cornea (11).

The globe (10) of the eye consists of three concentric coverings enclosing the various transparent media through which the light must pass before reaching the light-sensitive retina (12). The outermost covering is a fibrous protective portion the posterior five-sixths of which is white and opaque and called the sclera (13), and sometimes referred to as the white of the eye where visible to the front. The anterior one-sixth of this outer layer is the transparent cornea (11).

A middle covering is mainly vascular and nutritive in function and is comprised of the choroid, ciliary body (15) and iris (20). The choroid (14) generally functions to maintain the retina (12). The ciliary body (15) is involved in suspending the lens (17) and accommodation of the lens. The iris (16) is the most anterior portion of the middle covering of the eye and is arranged in a frontal plane. It is a thin circular disc similar in function to the diaphragm of a camera, and is perforated near its center by a circular aperture called the pupil (20). The size of the pupil varies to regulate the amount of light which reaches the retina (12). It contracts also to accommodation, which serves to sharpen the focus by diminishing spherical aberration. The iris divides the space between the .cornea (11) and the lens (17) into an anterior chamber (21) and posterior chamber. The innermost portion of covering is the retina (12), which is made up of nerve elements which form the true receptive portion for visual impressions.

The retina (12) is a part of the brain arising as an outgrowth from the fore-brain, with the optic nerve (23) serving as a fiber tract connecting the retina part of the brain with the fore-brain. A layer of rods and cones, lying just beneath a pigmented epithelium on the anterior wall of the retina serve as visual cells or photoreceptors which transform physical energy (light) into nerve impulses.

The vitreous body (24) is a transparent gelatinous mass which fills the posterior four-fifths of the globe (10). At its sides it supports the ciliary body (15) and the retina (12). A frontal saucer-shaped depression houses the lens.

The lens (17) of the eye is a transparent bi-convex body of crystalline appearance placed between the iris (16) and vitreous body (24). Its axial diameter varies markedly with accommodation. A ciliary zonule (25), consisting of transparent fibers passing between the ciliary body (15) and lens (17) serves to hold the lens (17) in position and enables the ciliary muscle to act on it.

Referring again to the cornea (11), this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards its periphery. Most of the refraction of the eye takes place at the cornea.

Figure 2:
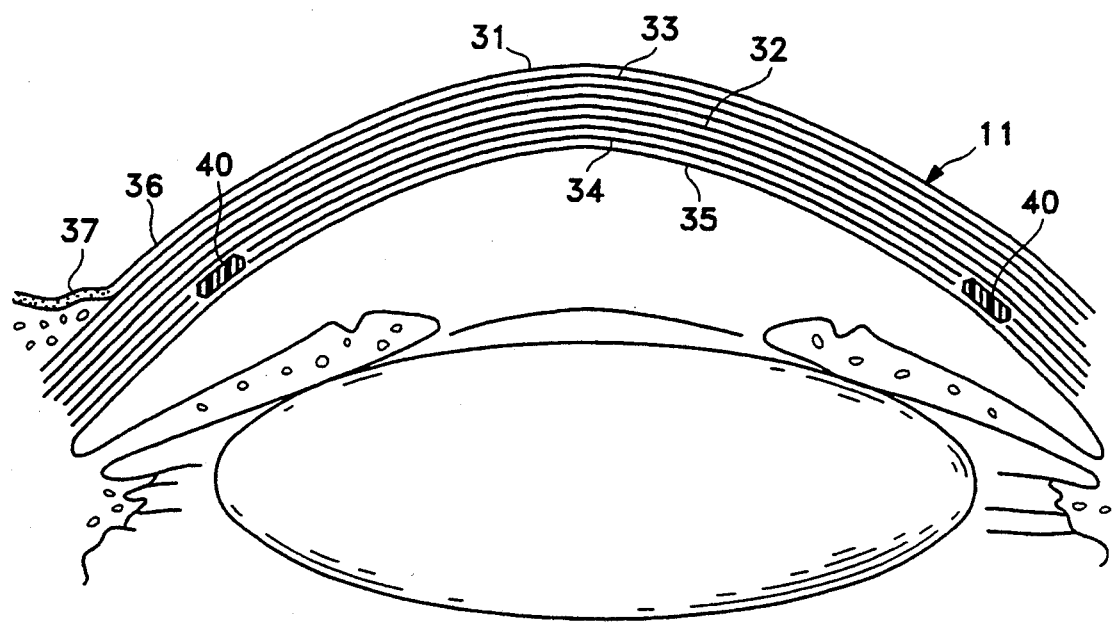
FIG. 2 is a schematic representation of the anterior portion of the eye showing the various layers of the cornea.

Referring to FIG. 2, a more detailed drawing of the anterior portion of the globe shows the various layers of the cornea (11) made up of an epithelium (31). Epithelial cells on the surface thereof function to maintain transparency of the cornea (11). These epithelial cells are rich in glycogen, enzymes, and acetylcholine and their activity regulates the corneal corpuscles and controls the transport of water and electrolytes through the lamellae of the stroma (32) of the cornea (11).

An anterior limiting lamina (33), referred to as Bowman's membrane or layer, is positioned between the epithelium (31) and the stroma (32) of the cornea. The stroma (32) is comprised of lamella having bands of fibrils parallel to each other and crossing the whole of the cornea. While most of the fibrous bands are parallel to the surface, some are oblique, especially anteriorly. A posterior limiting lamina (34) is referred to as Descemet's membrane. It is a strong membrane sharply defined from the stroma (32) and resistant to pathological processes of the cornea.

The endothelium (35) is the most posterior layer of the cornea and consists of a single layer of cells. The limbus (37) is the transition zone between the conjunctiva and sclera on the one hand and the cornea (11) on the other.

As has been explained above, most of the eye's refraction takes place at the outer portion of the cornea (12). The overall concept behind this invention is that by addition of selected amounts of bulk at the steeper portions of the anterior cornea or by inclusion of a non-uniform ring in radial tension, the anterior corneal surface will be forced into a generally spherical surface thereby correcting the undesired astigmatism.

Figure 3:
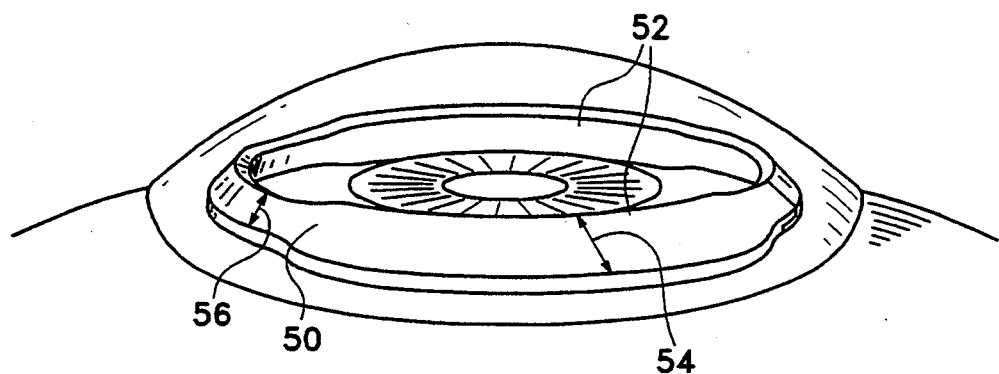
FIG. 3 depicts the inventive ACICR as it resides within the cornea.

FIG. 3 shows the placement of the non-regular ACICR within the cornea as discussed above. In this instance, the ring (50) has two regions (52) of added bulk or dimension. The larger regions in this instance have a larger relational width (54) than the local width of the narrower region (56). See also the side view of the comparative widths in FIG. 3. The relationship between the local widths (54) and (56), the thickness (58) at various positions of the ACICR, and their respective corrections, are known and may be determined from our U.S. patent application Ser. No. 07/820,472, filed Dec. 10, 1991.

Figure 5:
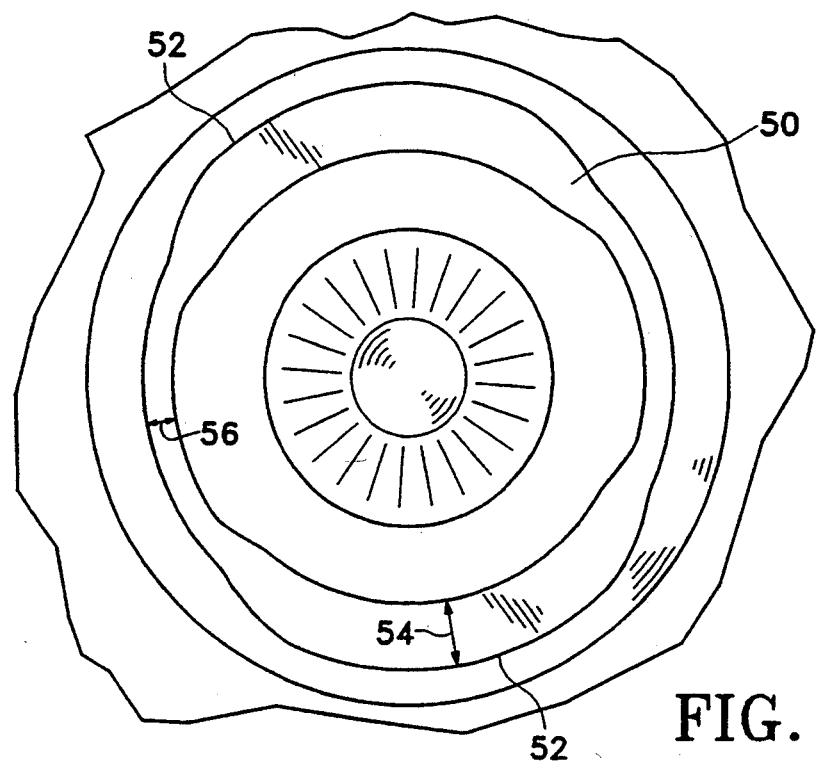
FIG. 5 is a frontal view showing the placement of the ACICR within the eye.

FIG. 5 is a frontal view of the eye having an ACICR installed. The ring (50) has two regions of added dimension (52). Those regions of added dimension would be placed in the regions of the cornea having the steepest slope in an effort to correct the cornea to an approximate spherical, or at least regular, shape about its anterior surface. The regions of added dimension are critically tailored to correct the astigmatism found in a particular eye. In general, the regions (52) subtend an arc of at least about 2° measured from the center of the ring. More typically, the regions of larger dimension will subtend 10° to about 180° of an arc on the ring. The larger values are to remedy such conditions as keratoconus in which (typically) a significant angular portion the cornea is thinned or, at least, significantly lower (flatter) in profile than other portions of the carnea. Such regions typically subtend 15° to 45° of the ring arc in correction of typical astigmatic conditions. Consequently, for most conditions, the arc should be at least about 2°, preferably about 10° to 90°, more preferably about 20° to 45°, all however tailored to correction of the noted astigmatism in a particular eye. Special corrections up to 340°, although typically of up to 180°, of subtended arc are acceptable when special circumstances of astigmatism are encountered.

When multiple sections of added dimension are used, each section may be of the subtended arc sizes listed above for the single arcs. Clearly though, the sum of all of the subtended arcs for the must be less than 350° or so.

Figure 4:
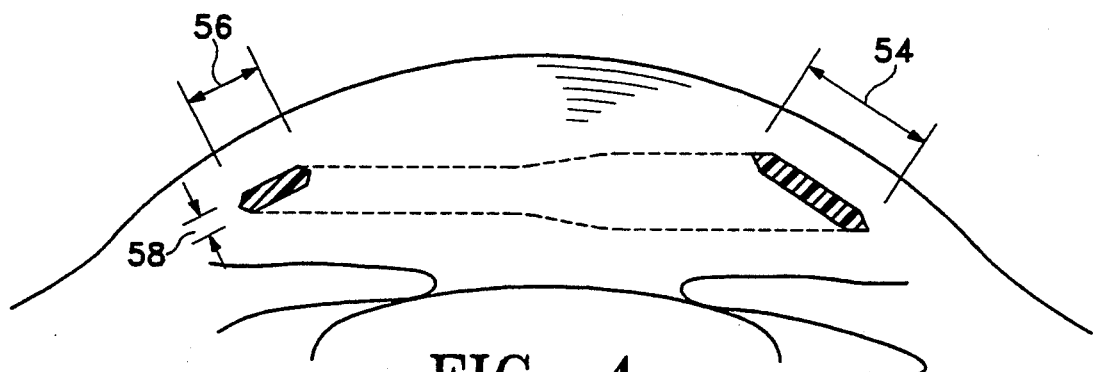
FIG. 4 is a side cross-section of the ACICR within the cornea.
Figure 6:
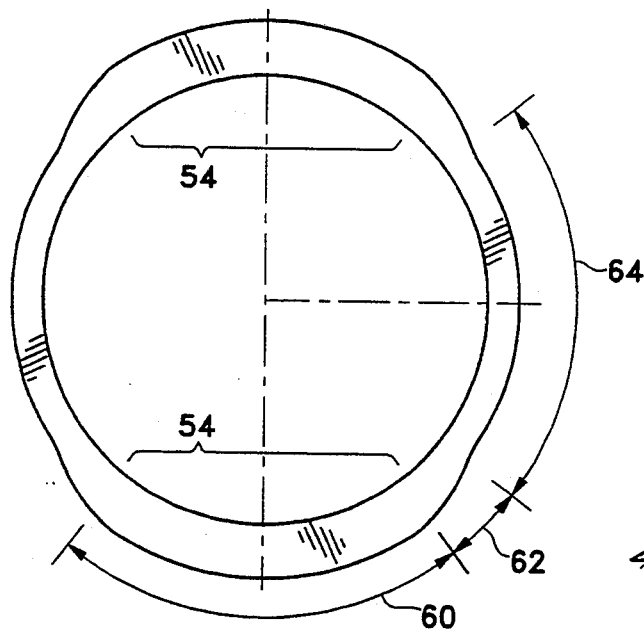
FIG. 6 is a frontal view of the ACICR having symmetrical areas of added bulk or cross-section.

FIG. 6 shows a frontal view of an ACICR in which the regions of added dimension are generally symmetrical. The regions of added dimension (54) are shown each to extend over a region of about 90° of the ACICR. FIG. 6 also shows a transition zone (62) between the area of added bulk 60 and the comparatively thinner region at (64). The transition zone allows the ACICR to be inserted into an intrastromal channel with greater ease. We believe this permits installation of the ACICR with less trauma. The arc (64) of lesser dimension is shown in FIG. 6. As with the local diameters (54)

and (56) of the ACICR as shown in FIGS. 3 and 4, the percentage of arcs (60) and (64) and their respective relationship to each other are a function of the level of astigmatism to be corrected. The percentage of arcs of the areas of added dimension (60) and (64) are of the same relative sizes as discussed above in relation to FIG. 5.

Figure 7:
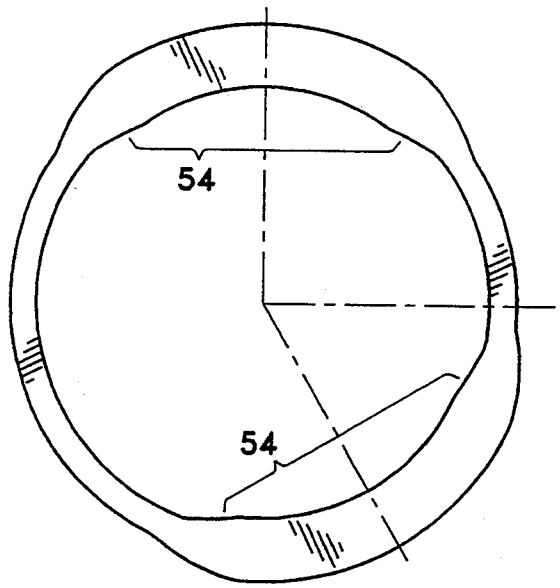
FIG. 7 is a frontal view of an ACICR having non-symmetric areas of added bulk or cross-section.

FIG. 7 shows an ACICR with regions of enhanced dimension which are not placed symmetrically about the ring. Again, such a ring would be employed in an eye which did not have symmetrical astigmatism about a single axis. Such an ACICR would be employed with the intent to bring the corneal shape back into general spherical form.

Figure 8:
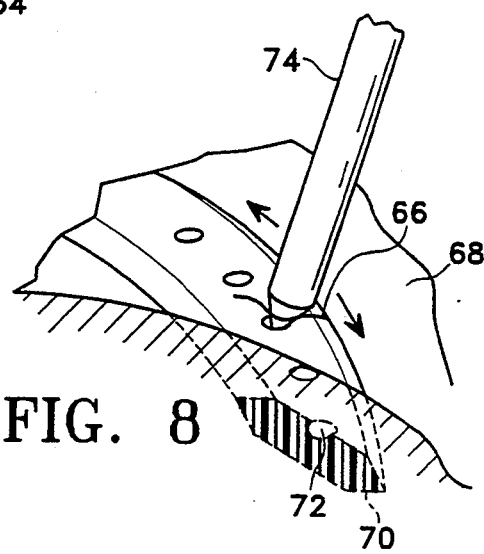
FIG. 8 depicts a feature of the invention which allows the ACICR to be manipulated into proper position for astigmatism correction.

The ring would be installed in the inner lamellar regions of the corneal stroma by any of the methods we have shown in the past to be suitable for such installation. Particularly desired is the process and its allied apparatus shown in U.S. Ser. No. 07/867,745, CORNEAL VACUUM CENTERING GUIDE AND DISSECTOR, filed Apr. 4, 1992, (attorney docket 25169-20006.00). In general, the ring is installed in the following manner: a small radial incision is made at the radius in which the ring is ultimately to be installed about the cornea. A dissector in the form of a split ring and having a point suitable for producing an interlamellar channel or tunnel in the corneal stroma is introduced through the small incision and rotated in such a fashion that a generally circular channel is formed completely about the cornea. The dissector is then rotated in the opposite direction to withdraw it from the tunnel thus formed. An ACICR is then introduced into the circular channel and joined at its ends. ICRs of constant cross-section typically need no further adjustment other than, perhaps, to move the point of junction away from the region of corneal incision so to help assure that the junction is held together by the interlamellar tension of the cornea. However, with an ACICR, the relationship of the ring and the astigmatic aberration must be aligned so to allow the ACICR to perform its desired correction. In FIG. 8, one such method for adjusting the position of the ACICR in the eye is shown. The radial incision (66) in cornea (68) which is used to introduce the ICR into the eye is shown. The ACICR (70) has a number of depressions (72) spaced about its upper surface. The position of the ACICR (70) is changed by engaging a generally pointed tool (74) into the depressions and slipping the ring (70) around in one direction or another until the regions of added dimension are in appropriate position for correcting the astigmatic aberrations of the cornea. Other variations on this will be apparent to those studying the need to adjust the position of these rings.

Figure 9A:
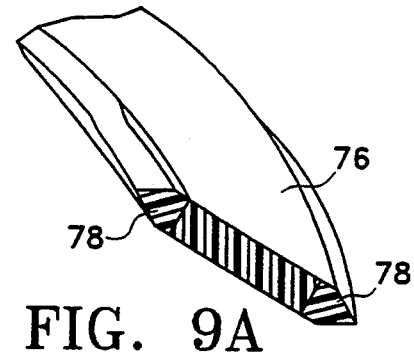
FIGS. 9A and 9B show a variation of the inventive ACICR using a composite ring in which a portion of the ring uses a swellable polymer.
Figure 9B:
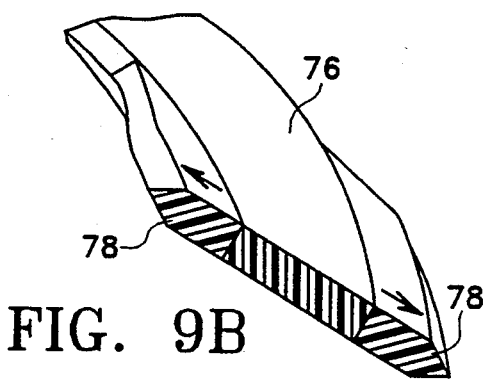

The materials used in these rings are typically stiff physiologically acceptable polymers such as polymethylmethacrylate (PMMA), TEFLON, polycarbonate, polyolefins such as polyethylene, polypropylene, polybutylene, and their mixtures and interpolymers, or a silicone polymer or interpolymer such as are known in the art to be appropriately used in hard contact lenses. PMMA has a long history in ophthalmological usage and consequently is quite desirable for use in these ACICRs. However, another desirable variation is shown in FIGS. 9A and 9B. In this variation, the added dimension comprises a polymer which is swellable or expands upon continued contact with water. For instance, FIG. 9A shows a cross-section of an ACICR having a central portion (76) of a polymer such as PMMA and two regions (78) bonded to the inner and outer periphery of central portion (76). Outer portions (78) may be made of a crosslinked polymeric gel such as polyhydroxyethylmethylacrylate (Poly-HEMA) or polyvinylpyrrolidone (PVP). The extent of crosslinking in these polymers determines the extent to which the polymers will swell upon being exposed to water. In general, the higher the extent of crosslinking, the lower the volume increase upon contact with water. Some materials used in soft contact lenses will contain up to 99% by volume water. In any event, FIG. 9A shows the bonded outer portions (78) in their dehydrated condition (if the polymer is not highly crosslinked) and FIG. 9B shows those same outlying portions after insertion into the cornea and after they have been allowed to hydrate and swell. This variation of the inventive ACICRs allows the device to be inserted at a much smaller size but allows the ring to swell to correct much larger aberrations.

Figure 10:
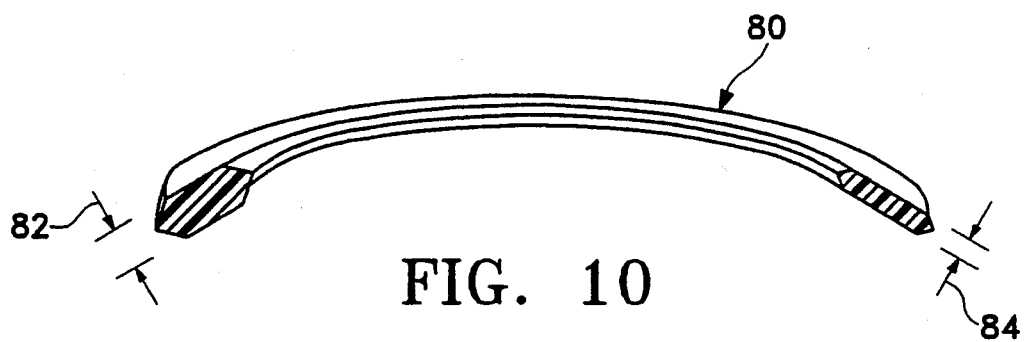
FIG. 10 shows an ACICR in which the thickness of the ring is varied.

The ACICR (80) shown in FIG. 10 is one in which the thickness of at least one portion of the regions is thicker (82) than another thinner portion (84) of the ring. As with the other ACICRs depicted in FIGS. 3–7, the number of thicker portions of the ring may be one or more depending upon the spherical aberration to be corrected. The typical ACICR likely will have two thicker regions about 180° apart on the ring. The ring may be between about 45° and more than about 140°. The portions of the arc which are thicker are also to be determined depending upon the astigmatism of the eye to be repaired.

Figure 11:
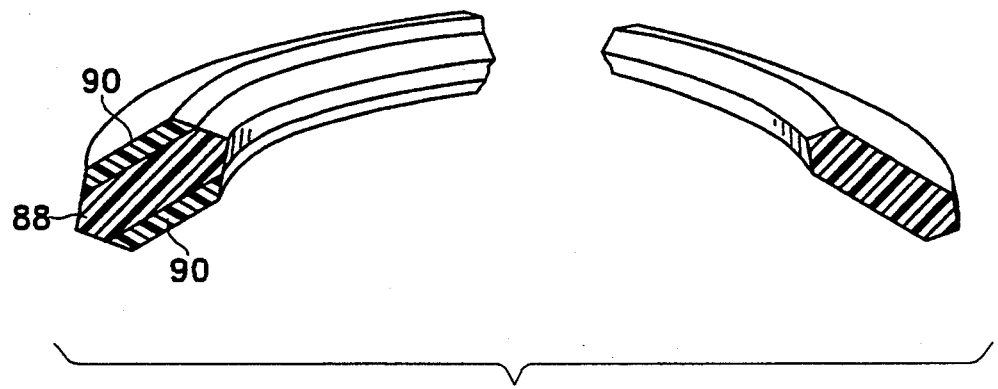
FIG. 11 shows an ACICR in which the ring is a composite of a stiff polymer and a swellable polymer.

FIG. 11 shows another variation of the ACICRs in which the ring is a composite assembly. The central portion (88) is of the one or more of the stiff polymers discussed above. The peripheral portions (90) comprise a swellable polymer which swells upon contact with moisture. As with the composite ACICRs above, they may be introduced into the eye prior to hydration, adjusted into proper position, and allowed to hydrate and swell into final shape.

The terms and expressions which have been used in the description above are used as terms of description and not of limitation. There is no intention of excluding equivalents of the features shown or described. It is recognized that one having ordinary skill in this art would perceive equivalents to the inventions claimed below which equivalents would be within spirit of the invention as expressed above.

I claim as my invention:

1. A split biocompatible polymeric ring for the correction of astigmatism in an eye having a cornea, which ring has a cross section, which ring is suitable for introduction into the corneal stroma and has a circumference sufficient to substantially encircle within the cornea, in which the cross section of the ring has at least two areas of comparatively larger dimension than other cross sections of the ring and allow the ring to be rotated in the cornea and where the areas of comparatively larger dimensions subtend more than about 2° of the arc of the ring and are selected to substantially correct said astigmatism.

2. The ring of claim 1 in which the cross-section has two areas of comparatively larger dimension.

3. The ring of claim 2 in which the regions of comparatively larger dimension are spaced apart on the circumference of the ring at an angle measured from the center of the ring between 45° and more than about 180°.

4. The ring of claim 3 in which the two areas of comparatively larger dimension are spaced on the circumference of the ring about 180° apart on the ring.

5. The ring of claim 2 in which the two areas of comparatively larger dimension are not symmetrical about the ring.

6. The ring of claim 1 in which the areas of larger cross section have transition regions to the areas of smaller dimension.

7. The ring of claim 1 additionally comprising adjusting means for positioning the ring in the eye.

8. The ring of claim 1 in which the cross section has more than two areas of comparatively larger cross-section.

9. The ring of claim 1 so that the ends of the split ring are joinable.

10. The ring of claim 1 comprising one or more physiologically acceptable polymers.

11. The ring of claim 10 where the polymer comprises polymethylmethacrylate.

12. The ring of claim 10 additionally comprising a swellable polymer.

13. The ring of claim 12 in which the swellable polymer is selected from polyhydroxyethylmethylacrylate and polyvinylpyrrolidone.

14. A split biocompatible polymeric ring for the correction of astigmatism in an eye having a cornea, which ring has a cross-section, which ring is suitable for introduction into a previously formed intrastromal channel encircling the cornea, has a circumference sufficient to substantially encircle within the cornea, in which the cross-section of the ring has at least one area of comparatively larger dimension and, in which the ring may be rotated within the previously formed intrastromal channel and allow the ring to be rotated in the cornea and where the areas of comparatively larger dimensions subtend more than about 2° of the arc of the ring and are selected to substantially correct said astigmatism.

15. The ring of claim 14 in which the cross-section has two areas of comparatively larger dimension.

16. The ring of claim 15 in which the regions of comparatively larger dimension are spaced apart on the circumference of the ring at an angle measured from the center of the ring between 45° and more than about 180°.

17. The ring of claim 16 in which the two areas of comparatively larger dimension are spaced on the circumference of the ring about 180° apart on the ring.

18. The ring of claim 15 in which the two areas of comparatively larger dimension are not symmetrical about the ring.

19. The ring of claim 14 in which the areas of larger dimension have transition regions to the areas of smaller dimension.

20. The ring of claim 14 additionally comprising adjusting means for positioning the ring in the eye.

21. The ring of claim 14 in which the cross-section has more than two areas of comparatively larger cross-section.

22. The ring of claim 14 so that the ends of the split ring are joinable.

23. The ring of claim 14 comprising one or more physiologically acceptable polymers.

24. The ring of claim 23 where the polymer comprises polymethylmethacrylate.

25. The ring of claim 23 additionally comprising a swellable polymer.

26. The ring of claim 25 in which the swellable polymer is selected from polyhydroxyethylmethylacrylate and polyvinylpyrrolidone.

* * * * *